(12) United States Patent
Muller

(10) Patent No.: US 8,298,597 B2
(45) Date of Patent: Oct. 30, 2012

(54) COMPOSITION TO HELP PROTECT A USER AGAINST LIVER DAMAGE FROM ALCOHOL CONSUMPTION

(76) Inventor: Charles Thomas Muller, Sunnyside, NY (US)

( * ) Notice: Subject to any disclaimer, the term of this patent is extended or adjusted under 35 U.S.C. 154(b) by 0 days.

(21) Appl. No.: 12/759,219

(22) Filed: Apr. 13, 2010

(65) Prior Publication Data

US 2011/0250298 A1  Oct. 13, 2011

(51) Int. Cl.
*A23L 1/302* (2006.01)
*A23L 1/303* (2006.01)
*A01N 59/02* (2006.01)

(52) U.S. Cl. ............................. 426/72; 426/73; 424/702
(58) Field of Classification Search ........................ None
See application file for complete search history.

(56) References Cited

U.S. PATENT DOCUMENTS

2007/0202215 A1* 8/2007 Lak .................................. 426/61
2009/0011054 A1* 1/2009 Ikonte et al. .................. 424/728

* cited by examiner

*Primary Examiner* — David J Blanchard
*Assistant Examiner* — Tigabu Kassa
(74) *Attorney, Agent, or Firm* — Michael Ries

(57) ABSTRACT

The present invention is a composition that can be taken by a user with an alcohol consuming lifestyle, to protect the user from liver damage as a result of consuming alcohol. The composition contains milk thistle extract, dandelion root, artichoke extract, vitamin E, selenium, thiamin, riboflavin, niacin, pyridoxine and cyanocobalamin. The alcohol is ethyl alcohol based drinks such as liquor, beer, wine or a combination of ethyl alcohol based drinks, liquor, beer or wine. The composition can be taken by a user in the form of a pill, a tablet or a capsule.

8 Claims, No Drawings

COMPOSITION TO HELP PROTECT A USER AGAINST LIVER DAMAGE FROM ALCOHOL CONSUMPTION

TECHNICAL FIELD & BACKGROUND

The present invention generally relates to a composition made up of a variety of vitamins, extracts, organic matter and lipoproteins. More specifically, the invention is a composition that helps protect a user against the negative effects from alcohol consumption.

It is an object of the invention to provide a composition to help protect a person from liver damage from alcohol consumption.

What is really needed is a composition that can be conveniently taken that can protect a person from liver damage as a result of long term alcohol consumption.

DETAILED DESCRIPTION OF EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

The composition of the present invention is one that can be taken by a user with an alcohol consuming lifestyle, to protect the user from liver damage as a result of consuming alcohol. An alcohol consuming lifestyle is one where the user drinks any type of ethyl alcohol based drink such as liquor, beer, wine or a combination of any ethyl alcohol based drink, liquor, beer or wine on a regular basis. However, this composition is also designed for people who consume an average of more than 10 drinks per week, who want protection from liver damage from long term alcohol consumption.

The composition can be in a pill form, a tablet form or a capsule form and contains the following ingredients that have been scientifically proven to help battle free radicals and toxins that are harmful to the liver. The first ingredient is milk thistle extract, which is used to aid liver, gallbladder and kidney function and has been known and used for over 2,000 years. Milk thistle extract also helps prevent cirrhosis and damage from free radicals and is recommended by liver specialists worldwide and is well known to those skilled in the art. The second ingredient is dandelion root, which helps protect and heal damaged liver cells, promote new liver cell growth and strengthen the user's immune system. This ingredient assists the flow of bile to the gallbladder, prevents gallstone formation and purifies the liver and all its functions. Like dandelion root, the composition also contains artichoke extract, which also cleanses and purifies the liver, promotes healthy bile flow to the gallbladder and helps prevent gallstones. The composition also contains vitamin E, which is a powerful anti-oxidant that helps prevent liver disease, protects red blood cells and helps prevent free radical damage to cell membranes that your body needs to properly function. The composition also contains another anti-oxidant, selenium, which discourages the development of a fatty liver and cirrhosis. When combined with vitamin E, these two anti-oxidants work together and further enhance their individual protective capabilities to help keep a user's liver healthy.

The composition also contains thiamin, which is used to help transform sugar into energy. Without thiamin, nerves do not function properly and a plethora of mental and metabolic problems can evolve and can result in lactic acidosis, abnormal heartbeat, heart failure, impotency, deteriorating memory capability and other mental disorders. The composition also contains riboflavin, that helps prevent the feeling of exhaustion and fatigue after a heavy night of drinking. This is also an important ingredient since people who drink on a regular basis are almost always deficient in riboflavin. This protein is essential to help a person's body properly process both food and alcohol. Another important ingredient in the composition is niacin, which builds enzymes needed to process alcohol. Without niacin, both alcohol and food are processed improperly in the intestines and a person could experience indigestion and diarrhea, as well as the possibility of dermatitis and various mental difficulties. Another ingredient in the composition is pyridoxine, which makes lipoproteins that transport cholesterol and fat. Pyridoxine can also help prevent a fatty liver and poor metabolism, poor niacin, protein and amino acid formation, decreased immunity, hypoglycemia and poor liver repair. Another ingredient of the composition is the vitamin cyanobalamin, which generally protects a user's liver. A deficiency in this essential vitamin can also cause nervous disorders, bleeding gums, fatigue and numerous other unpleasant symptoms.

The composition combines all of these vitamins, extracts, organic matter and lipoproteins in one easy to take and convenient pill, tablet or capsule. There is no mixing and matching pills and no trying to remember what to take and when to take each of the individual ingredients of the composition. A user just takes one pill, tablet or capsule once a day while maintaining an alcohol consuming lifestyle and one more on days when the user is actually drinking, before going to bed at night.

A method of using and taking the composition to protect a user who has an alcohol consuming lifestyle from liver damage as a result of consuming alcohol includes consuming the composition once a day while having an alcohol drinking lifestyle, consuming the composition before going to bed on days when the user consumes alcohol and terminating usage of the composition once the user's alcohol drinking lifestyle is terminated. The user would use the composition in the previously described pill, tablet or capsule form. Alcohol, as previously described, is any type of ethyl alcohol based drink such as liquor, beer, wine or a combination of any ethyl alcohol based drink, liquor, beer or wine.

EXAMPLE #1

The following example further illustrates the composition but should not be construed as in any way limiting its scope. Example #1 includes the following formulation range (by weight):

50-400 mg of milk thistle extract
20-300 mg of dandelion root
20-300 mg of artichoke extract
50-600 IU of vitamin E
25-300 mcg of selenium
10-100 mg of thiamin
10-100 mg of riboflavin
10-100 mg of niacin
10-100 mg pyridoxine and
10-100 mcg of cyanocobalamin)

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A composition to protect a user from liver damage as a result of consuming alcohol, comprising:
   400 mg of milk thistle extract;
   300 mg of dandelion root;
   20 mg of artichoke extract;
   600 IU of vitamin E;
   300 mcg of selenium;
   100 mg of thiamin;
   100 mg of riboflavin;
   100 mg of niacin;
   100 mg pyridoxine; and
   100 mcg of cyanocobalamin.

2. The composition according to claim 1, wherein said alcohol is liquor.

3. The composition according to claim 1, wherein said composition is in a pill form.

4. The composition according to claim 1, wherein said composition is in a tablet form.

5. The composition according to claim 1, wherein said user consumes said composition before going to bed only on days when said user has consumed said alcohol.

6. The composition according to claim 1, wherein said alcohol is beer.

7. The composition according to claim 1, wherein said alcohol is wine.

8. The composition according to claim 1, wherein said alcohol is a combination of liquor, beer and wine.

* * * * *